United States Patent
Moskowitz et al.

(10) Patent No.: US 10,016,225 B2
(45) Date of Patent: Jul. 10, 2018

(54) BI-DIRECTIONAL FIXATING TRANSVERTEBRAL BODY SCREWS, ZERO-PROFILE HORIZONTAL INTERVERTEBRAL MINIPLATES, TOTAL INTERVERTEBRAL BODY FUSION DEVICES, AND POSTERIOR MOTION-CALIBRATING INTERARTICULATING JOINT STAPLING DEVICE FOR SPINAL FUSION

(71) Applicant: Moskowitz Family LLC, Rockville, MD (US)

(72) Inventors: Nathan C. Moskowitz, Rockville, MD (US); Mosheh T. Moskowitz, Rockville, MD (US); Daniel Glozman, Kfar Adumim (IL)

(73) Assignee: Moskowitz Family LLC, Rockville, MD (US)

( * ) Notice: Subject to any disclaimer, the term of this patent is extended or adjusted under 35 U.S.C. 154(b) by 0 days.

(21) Appl. No.: 14/299,711

(22) Filed: Jun. 9, 2014

(65) Prior Publication Data

US 2015/0105824 A1 Apr. 16, 2015

Related U.S. Application Data

(60) Continuation of application No. 12/868,451, filed on Aug. 25, 2010, now Pat. No. 8,747,444, which is a
(Continued)

(51) Int. Cl.
*A61B 17/70* (2006.01)
*A61B 17/064* (2006.01)
(Continued)

(52) U.S. Cl.
CPC ........ *A61B 17/7064* (2013.01); *A61B 17/068* (2013.01); *A61B 17/0642* (2013.01);
(Continued)

(58) Field of Classification Search
CPC .... A61F 2/4455; A61F 2/4611; A61F 2/4405; A61F 2/442; A61F 2310/00029;
(Continued)

(56) References Cited

U.S. PATENT DOCUMENTS 4,064,881 A * 12/1977 Meredith ................ A61F 6/204
128/830
4,554,914 A 11/1985 Kapp et al.
(Continued)

FOREIGN PATENT DOCUMENTS

WO 2004093749 A1 11/2004
WO 2006091503 A1 8/2006

OTHER PUBLICATIONS

Vincent C. Traynelis, "Prosthetics and Biologics: The Wave of the Future," Clinical Neurosurgery, vol. 50, Proceedings of the Congress of Neurological Surgeons, Philadelphia, PA 2002, Chapter 9, pp. 207-219.
(Continued)

*Primary Examiner* — Pedro Philogene
(74) *Attorney, Agent, or Firm* — Fish & Richardson P.C.

(57) ABSTRACT

An apparatus and method for joining members together using a self-drilling screw apparatus or stapling apparatus are disclosed. The screw apparatus includes a worm drive screw, a spur gear and superior and inferior screws which turn simultaneously in a bi-directional manner. A rotating mechanism drives the first and second screw members in opposite directions and causes the screw members to embed themselves in the members to be joined. The screw apparatus can be used to join members such as bones, portions of
(Continued)

the spinal column, vertebral bodies, wood, building materials, metals, masonry, or plastics. A device employing two screws (two-in-one) can be combined with a capping horizontal mini-plate. A device employing three screws can be combined in enclosures (three-in-one). The stapling apparatus includes grip handles, transmission linkages, a drive rod a fulcrum and a cylinder. The staple has superior and inferior segments with serrated interfaces, a teethed unidirectional locking mechanism and four facet piercing elements. The staples can be also be used to join members such as bones, portions of the spinal column, or vertebral bodies.

16 Claims, 18 Drawing Sheets

Related U.S. Application Data division of application No. 11/536,815, filed on Sep. 29, 2006, now Pat. No. 7,846,188, which is a continuation-in-part of application No. 11/208,644, filed on Aug. 23, 2005, now Pat. No. 7,704,279.

(60) Provisional application No. 60/670,231, filed on Apr. 12, 2005.

(51) Int. Cl.
  *A61B 17/068* (2006.01)
  *A61F 2/46* (2006.01)
  *A61F 2/44* (2006.01)
  *A61F 2/30* (2006.01)

(52) U.S. Cl.
  CPC ............ *A61B 17/70* (2013.01); *A61F 2/4455* (2013.01); *A61F 2/4611* (2013.01); *A61B 2017/0648* (2013.01); *A61F 2/442* (2013.01); *A61F 2/4405* (2013.01); *A61F 2002/30507* (2013.01); *A61F 2002/30517* (2013.01); *A61F 2002/30525* (2013.01); *A61F 2002/30579* (2013.01); *A61F 2002/30828* (2013.01); *A61F 2002/30841* (2013.01); *A61F 2002/30904* (2013.01); *A61F 2002/448* (2013.01); *A61F 2002/4627* (2013.01); *A61F 2002/4628* (2013.01); *A61F 2220/0025* (2013.01); *A61F 2310/00023* (2013.01); *A61F 2310/00029* (2013.01)

(58) Field of Classification Search
  CPC .... A61F 2310/00023; A61F 2220/0025; A61F 2002/30507; A61F 2002/30517; A61F 2002/30525; A61F 2002/30579; A61F 2002/30828; A61F 2002/30841; A61F 2002/30904; A61F 2002/448; A61F 2002/4627; A61F 2002/4628
  USPC .... 606/72, 75, 115, 151, 154–159, 215–222, 606/246–281, 300; 623/17.11–17.16
  See application file for complete search history.

(56) References Cited

U.S. PATENT DOCUMENTS

| | | | |
|---|---|---|---|
| 4,599,086 A | 7/1986 | Doty | |
| 4,636,217 A | 1/1987 | Ogilvie et al. | |
| 4,960,420 A | 10/1990 | Goble et al. | |
| 4,997,432 A | 3/1991 | Keller | |
| 5,005,749 A | 4/1991 | Aranyi | |
| 5,062,850 A | 11/1991 | MacMillan et al. | |
| 5,123,926 A | 6/1992 | Pisharodi | |
| 5,290,312 A | 3/1994 | Kojimoto et al. | |
| 5,405,391 A | 4/1995 | Henderson et al. | |
| 5,413,583 A | 5/1995 | Wohlers | |
| 5,454,819 A | 10/1995 | Knoepfler | |
| 5,514,180 A | 5/1996 | Heggeness et al. | |
| 5,660,188 A | 8/1997 | Groiso | |
| 5,667,472 A | 9/1997 | Finn et al. | |
| 5,713,912 A * | 2/1998 | Porter | A61B 17/122 606/151 |
| 5,782,832 A | 7/1998 | Larsen et al. | |
| 5,865,848 A | 2/1999 | Baker | |
| 5,868,759 A * | 2/1999 | Peyser | A61B 17/1285 227/901 |
| 5,888,223 A | 3/1999 | Bray, Jr. | |
| 5,916,224 A | 6/1999 | Esplin | |
| 5,951,574 A * | 9/1999 | Stefanchik | A61B 17/1285 227/901 |
| 5,960,522 A | 10/1999 | Boe | |
| 5,968,054 A | 10/1999 | Yeatts et al. | |
| 5,976,136 A * | 11/1999 | Bailey | A61B 17/6458 606/301 |
| 6,126,689 A | 10/2000 | Brett | |
| 6,342,074 B1 | 1/2002 | Simpson | |
| 6,368,350 B1 | 4/2002 | Erickson et al. | |
| 6,375,682 B1 | 4/2002 | Fleischmann et al. | |
| 6,419,704 B1 | 7/2002 | Ferree | |
| 6,432,106 B1 | 8/2002 | Fraser | |
| 6,458,159 B1 | 10/2002 | Thalgott | |
| 6,527,804 B1 | 3/2003 | Gauchet et al. | |
| 6,533,818 B1 | 3/2003 | Weber et al. | |
| 6,558,423 B1 | 5/2003 | Michelson | |
| 6,572,653 B1 | 6/2003 | Simonson | |
| 6,579,318 B2 | 6/2003 | Varga et al. | |
| 6,582,468 B1 | 6/2003 | Gauchet | |
| 6,613,055 B2 | 9/2003 | Di Emidio | |
| 6,629,998 B1 | 10/2003 | Lin | |
| 6,641,614 B1 | 11/2003 | Wagner et al. | |
| 6,719,794 B2 | 4/2004 | Gerber | |
| 6,723,126 B1 | 4/2004 | Berry | |
| 6,733,532 B1 | 5/2004 | Gauchet et al. | |
| 6,764,491 B2 | 7/2004 | Frey et al. | |
| 6,770,094 B2 | 8/2004 | Fehling et al. | |
| 6,824,564 B2 | 11/2004 | Crozet | |
| 6,852,117 B2 * | 2/2005 | Orlowski | A61B 17/122 606/120 |
| 6,904,308 B2 | 6/2005 | Frisch et al. | |
| 6,953,477 B2 | 10/2005 | Berry | |
| 6,955,671 B2 | 10/2005 | Uchikubo | |
| 6,972,019 B2 | 12/2005 | Michelson | |
| 7,030,904 B2 | 4/2006 | Adair et al. | |
| 7,033,394 B2 | 4/2006 | Michelson | |
| 7,037,258 B2 | 5/2006 | Chatenever et al. | |
| 7,097,615 B2 | 8/2006 | Banik et al. | |
| 7,211,112 B2 | 5/2007 | Baynham et al. | |
| 7,326,248 B2 | 2/2008 | Michelson | |
| 7,442,209 B2 | 10/2008 | Michelson | |
| 7,615,059 B2 | 11/2009 | Watschke et al. | |
| 7,727,246 B2 | 6/2010 | Sixto et al. | |
| 7,862,616 B2 | 1/2011 | Lechmann et al. | |
| 8,034,060 B2 | 10/2011 | Keren et al. | |
| 8,328,872 B2 | 12/2012 | Duffield et al. | |
| 8,403,986 B2 | 3/2013 | Michelson | |
| 8,747,444 B2 * | 6/2014 | Moskowitz | A61B 17/0642 606/279 |
| 8,920,438 B2 * | 12/2014 | Aranyi | A61B 17/12 606/142 |
| 2002/0068977 A1 | 6/2002 | Jackson | |
| 2002/0143338 A1 | 10/2002 | Orbay et al. | |
| 2004/0088054 A1 | 5/2004 | Berry | |
| 2004/0177531 A1 | 9/2004 | DiBenedetto et al. | |
| 2004/0254644 A1 | 12/2004 | Taylor | |
| 2005/0027362 A1 | 2/2005 | Williams et al. | |
| 2005/0049590 A1 | 3/2005 | Alleyne et al. | |
| 2005/0177235 A1 | 8/2005 | Baynham et al. | |
| 2005/0216084 A1 | 9/2005 | Fleischmann | |
| 2005/0273170 A1 | 12/2005 | Navarro et al. | |
| 2005/0278026 A1 | 12/2005 | Gordon et al. | |
| 2007/0213820 A1 | 9/2007 | Magerl et al. | |

(56) References Cited

U.S. PATENT DOCUMENTS

2009/0105831 A1   4/2009  Jones et al.
2010/0145460 A1   6/2010  McDonough et al.

OTHER PUBLICATIONS

E.K. Wai et al., "Disk Replacement Arthroplasties: Can the Success of Hip and Knee Replacements be Repeated in the Spine?," Seminars in Spine Surgery, vol. 15, No. 4 (Dec.) 2003, pp. 473-482.
Richard A Guyer et al., "Intervertebral Disc Prostheses," Spine Journal, vol. 28, No. 15S, Supp. To Aug. 1, 2003, pp. S15-S23.
Dieter Grob et al., "Clinical Experience With the Dynesys Semirigid Fixation System for the Lumbar Spine," Spine, vol. 30, No. 3, 2005, pp. 324-331.
International Search Report (ISR) and Written Opinion of the International Searching Authority, dated Dec. 3, 2007, International Application No. PCT/US 07/05005.
International Search Report (ISR) and Written Opinion of the International Searching Authority, dated May 21, 2008, International Application No. PCT/US2007/021015.
International Search Report (ISR) and Written Opinion of the International Searching Authority, dated Jul. 9, 2008, International Application No. PCT/US2007021013.

* cited by examiner

BI-DIRECTIONAL FIXATING TRANSVERTEBRAL BODY SCREWS, ZERO-PROFILE HORIZONTAL INTERVERTEBRAL MINIPLATES, TOTAL INTERVERTEBRAL BODY FUSION DEVICES, AND POSTERIOR MOTION-CALIBRATING INTERARTICULATING JOINT STAPLING DEVICE FOR SPINAL FUSION

The present Application is a Continuation Application of U.S. patent application Ser. No. 12/868,451 filed Aug. 25, 2010, which is a Divisional Application of U.S. patent application Ser. No. 11/536,815 filed on Sep. 29, 2006, now U.S. Pat. No. 7,846,188 issued Dec. 7, 2010, which is a Continuation-In-Part Application of U.S. patent application Ser. No. 11/208,644, filed on Aug. 23, 2005, now U.S. Pat. No. 7,704,279 issued on Apr. 27, 2010, for which priority is claimed under 35 U.S.C. § 120; and this application also claims priority under 35 U.S.C. § 119(e) of U.S. provisional application No. 60/670,231, filed on Apr. 12, 2005; the entire contents of all the above identified patent applications are hereby incorporated by reference.

FIELD OF INVENTION

The present invention relates to a unique universal bidirectional screw (UBS) system, and in particular its application to the spine, also referred to as bi-directional fixating transvertebral (BDFT) screws which can be used to supplement other intervertebral spacers and/or bone fusion materials. BDFT screws can be incorporated into anterior and/or posterior cervical, thoracic and lumbosacral, novel, zero-profile, horizontal intervertebral mini-plates, and anterior cervical, thoracic and lumbosacral total interbody fusion devices (IBFD). In the lumbosacral and thoracic spine, BDFT screws can be used independently or supplemented with the horizontal intervertebral mini-plate or total IBFD, and are thus considered stand alone intervertebral body fusion constructs which may obviate the need for supplemental pedicle screw fixation. In the cervical spine these devices obviate the need for supplemental vertically oriented anterior plating, and can be used as stand alone interbody fusion devices. The present invention also relates to a stand-alone or supplemental, calibrating interarticular joint stapling device which can incrementally fine-tune posterior interarticular joint motion.

DESCRIPTION OF THE RELEVANT ART

Segmental spinal fusions which stabilize two or more adjacent segments of the spine are performed for painful degenerative disc disease, recurrent disc herniations, spinal stenosis, spondylolysis and spondylolisthesis. Over the past several decades a wide variety of fusion techniques and instrumentation have evolved. One of the earliest posterior fusion techniques entails non-instrumented in-situ on-lay posteriolateral fusion utilizing autologous iliac crest bone. Because of the high rate of imperfect fusions i.e. pseudoarthroses, transpedicular pedicle screw fixation which utilizes a variety of rods and interconnectors were developed to achieve less interbody motion and hence higher fusion rates. Pedicle screw fixation was initially combined with on-lay posteriolateral fusion. Because of the poor blood supply of the transverse processes, issues still remained with pseudoarthroses. In an attempt to address this problem, pedicle screw fixation has been supplemented with a variety of interbody fusion devices. This is based on the concept that axial loading enhances fusion and that the vertebral endplates have a better blood supply. Interbody lumbar fusion devices can be placed anteriorly via an anterior lumbar interbody fusion technique (ALIF) or posteriorly via a posterior lumbar interbody fusion technique (PLIF). Material options for interbody fusion devices have included autologous iliac crest/laminar bone, cylindrical threaded titanium interbody cages, cylindrical threaded cortical bone dowels, vertebral interbody rings or boxes, carbon fiber cages, or femoral ring allograft. To lessen the complication of prolonged nerve root retraction the technique of circumferential transforaminal lumbar interbody fusion technique (TLIF) has been introduced. This employs the transforaminal placement of an interbody spacer such as one kidney bean shaped allograft, two circular allografts, one or two titanium circular cages, a single titanium or Peek (polyether-ketone) boomerang spacer. The threaded spacers are usually supplemented with autologous bone and/or bone morphogenic protein (BMP), demineralized bone matrix (DBM) in the form of paste or cement, rh-BMP with collagen sponges, or similar osteoinductive biological agents which are known to enhance fusion.

Currently all lumbosacral fusion techniques, ALIF, PLIF and TLIF, are typically supplemented by pedicle screw placement. In addition posterior transfacet screws also have been used to supplement ALIF procedures. Complications of pedicle screw placement include duration of procedure, significant tissue dissection and muscle retraction, misplaced screws with neural and/or vascular injury, excessive blood loss, need for transfusions, prolonged recovery, incomplete return to work, excess rigidity leading to adjacent segmental disease requiring further fusions and re-operations. Further advances of pedicle screw fixation including minimally invasive and image-guided technology, and the development of flexible rods have imperfectly addressed some but not all of these issues. Transfacet screws and similar embodiments entail the use of short or long screws which provide static facet alignment without motion calibration.

Complications of all current interbody fusion devices is their lack of coverage of the majority of the cross sectional area of the vertebral endplates and their potential for extrusion. The recently described flexible fusion system which consists of flexible rods attached to transpedicular screws (Dionysis, Zimmer) suffers from a high pull-out rate, higher rate of re-operation than standard fusions, and does not rank high with patient satisfaction. See for example, *Clinical experience with the Dynesys semirigid fixation system for the lumbar spine: Surgical and patient-oriented outcome in 50 cases after an average of 2 years*; D, Grob, A. Benini and A. F. Mannion. Spine Volume 30, number 3, Feb. 1, 2005.

Single or multiple level anterior cervical spinal fusions typically employ the replacement of the cervical disc or discs with autologous or allograft bone, or an intervertebral spacer filled with autologous or allograft bone, demineralized bone matrix, BMP or rh-BMP etc. Currently these anterior cervical fusions are augmented with anterior vertical titanium plates which cross the intervertebral space or spaces and are secured to the vertebral bodies above and below the disc space or spaces with perpendicularly penetrating vertebral body screws. The purpose of these plates is to serve as a barrier to prevent extrusion of the intervertebral disc replacement. Recently anterior vertical plating has also been employed in anterior lumbar fusion.

Complications of anterior spinal plating include the potential for neurovascular injury with screw misplacement, screw and/or plate pull-out, and screw and/or plate breakage. Other complications include potential esophageal compression/injury in the cervical spine secondary to high plate profile or pull-out, and to potential devastating vascular injury in the lumbar spine with plate movement and/or dislodgement into anterior iliac vasculature. Recent advances in cervical plating have therefore concentrated on the creation of lower profile plates and even resorbable plates. These advances, however, have not eliminated the possibility of plate dislodgement and screw back out/breakage.

Objects of the Invention

To achieve segmental fusion, applicants propose the use of novel bi-directional fixating transvertebral (BDFT) screws which can be strategically inserted via anterior or posterior surgical spinal approaches into the anterior and middle columns of the intervertebral disc space. The BDFT mechanism employs turning a wormed driving screw which then turns a spur gear which in turn simultaneously turns a rostrally oriented screw into the cephalad vertebral body, and a caudally directed screw into the caudal vertebral body. The vertebral bodies above and below the disc space by virtue of their engagement and penetration by the BDFT screws are thus linked and eventually fused. The gear box casings of the BDFT screws prevent vertebral body subsidence. The inside of the denuded intervertebral space can then be packed with autologous or allograft bone, BMP, DBX or similar osteoinductive material. Posteriorly or anteriorly in the lumbar spine, these screws can be capped with a horizontal mini-plate which will prevent bony growth into the thecal sac and nerves. We refer to this as a two-in-one design i.e. two BDFT screws combined with one horizontal mini-plate. Anteriorly a total intervertebral spacer containing three BDFT screws can be inserted. We refer to this as a three-in-one design i.e. three BDFT screws in one total fusion construct, i.e. an IBFD.

Applicants postulate that BDFT screws provide as strong or stronger segmental fusion as pedicle screws without the complications arising from pedicle screw placement which include screw misplacement with potential nerve and/or vascular injury, violation of some healthy facets, possible pedicle destruction and blood loss. By placing screws across the intervertebral space from vertebral body to vertebral body engaging anterior and middle spinal columns, and not into the vertebral bodies via the transpedicular route, some of the healthy facet joints are preserved. Because this technique accomplishes both anterior and middle column fusion, without rigidly fixing the posterior column, it in essence creates a flexible fusion. This device therefore is a flexible fusion device because the preserved posterior joints retain their function achieving at least a modicum of mobility and hence a less rigid (i.e. a flexible) fusion.

The very advantage of trans-pedicular screws which facilitate a strong solid fusion by rigidly engaging all three spinal columns (anterior, middle and posterior), is the same mechanical mechanism whereby complete inflexibility of all columns is incurred thereby leading to increasing rostral and caudal segmental stress which leads to an increased rate of re-operation.

Transvertebral fusion also leads to far less muscle retraction, blood loss, and significant reduction in O.R. time. Thus the complication of pedicular screw pull-out and hence high re-operation rate associated with the current embodiment of flexible fusion pedicle screws/rods is obviated. The lumbosacral BDFT screws can be introduced via PLIF, TLIF or ALIF operative techniques. Although one can opt to supplement these screws with transpedicular screws there would be no absolute need for supplemental pedicle screw fixation with these operative techniques.

Bi-directional fixating transvertebral (BDFT) screws can also be combined with novel zero-profile horizontal cervical and lumbar mini-plates. They can also be combined with a total IBFD with insertion spaces for bone material insertion.

For the performance of anterior cervical, and lumbar anterior or posterior fusions one or two centrally placed BDFT screws anterior to an interverterbal graft or spacer, may be a sufficient barrier by itself to prevent device/graft extrusion. However, to further safeguard against graft/spacer extrusion, applicants have devised horizontal linear mini-plates which can be incorporated into two anteriorly placed BDFT screws. It can also be incorporated into two posteriorly BDFT screws which are inserted posteriorly, in addition to a third BDFT screw which has been inserted centrally and posteriorly. This achieves a total disc intervertebral construct placed posteriorly composed of three BDFT screws placed in a triangulating matter. The capping horizontal mini-plate would prevent the bony material which is packed into the interspace from growing into the ventral; aspect of the nerves. The horizontal linear mini-plates traverse the diameter of the disc space and most of the disc space height. Thus a horizontal mini-plate placed posteriorly immediately beneath the lumbosacral thecal sac and nerve roots which is capped and secured to right and left BDFT screws, would prevent intervertebral device/graft extrusion. This mini-plate is essentially a zero- to sub-zero-profile plate in that it is either flush with or below the rostral and caudal vertebral body surfaces.

Because the BDFT screws engage a small percentage of the rostral and caudal vertebral body surface area, this plating system could be performed at multiple levels. This plating system which utilizes BDFT screws in the anterior cervical spine does not lead to any esophageal compression/injury, or vascular iliac vein injury in the lumbar spine. For the performance of two or three level intervertebral fusion with horizontal mini-plates there is virtually no possibility of plate breakage which can occur in long vertical anterior plates which are in current usage. Similarly, screw dislodgement, if it occurs would lead to minimal esophageal compression or injury compared to large vertical plate/screw dislodgement. In addition, in the cervical spine BDFT screw placement closer to the midline would avert any possibility of lateral neural or vertebral artery injury. Likewise multiple placement of IBFD devices can also be performed without the above mentioned risks and complications.

If one were inclined to further enhance posterior column thoraco-lumbosacral fixation, applicants introduce a novel calibrated facet stapling device which staples the inferior articulating facet of the superior segment to the superior articulating facet of the caudal vertebral segment unilaterally or bilaterally, further minimizing motion until interbody fusion occurs. The degree of flexibility can be further modulated by varying the calibration strength and torque of facet stapling. This would be dictated by the need for greater or lesser degrees of motion preservation. All other know transfacet stabilizers are not calibrated, but are static.

Currently, failed anterior lumbar arthoplasties are salvaged by combined anterior and posterior fusions. BDFT screws and/or IBFDs could be utilized as a one-step salvage operation for failed/extruded anteriorly placed lumbar artificial discs obviating the above salvage procedures which have greater morbidity. Likewise, for anterior cervical fusion, applying cervical BDFT screws alone or in combination with cervical mini-plates or IBFDs addresses the deficiencies and complications of current cervical plating technology as mentioned above.

BRIEF DESCRIPTION OF THE DRAWINGS

FIG. 12 illustrates the different components of the staple gun.

DETAILED DESCRIPTION OF THE INVENTION

1. The Medical Device

Referring to FIGS. 1A-5C the above described problem can be solved in the cervical, thoracic and lumbar spine by insertion into the denuded intervertebral disc space a bi-directional fixating transvertebral (BDFT) screw or (UBS) screws 100.

Figure 1A:
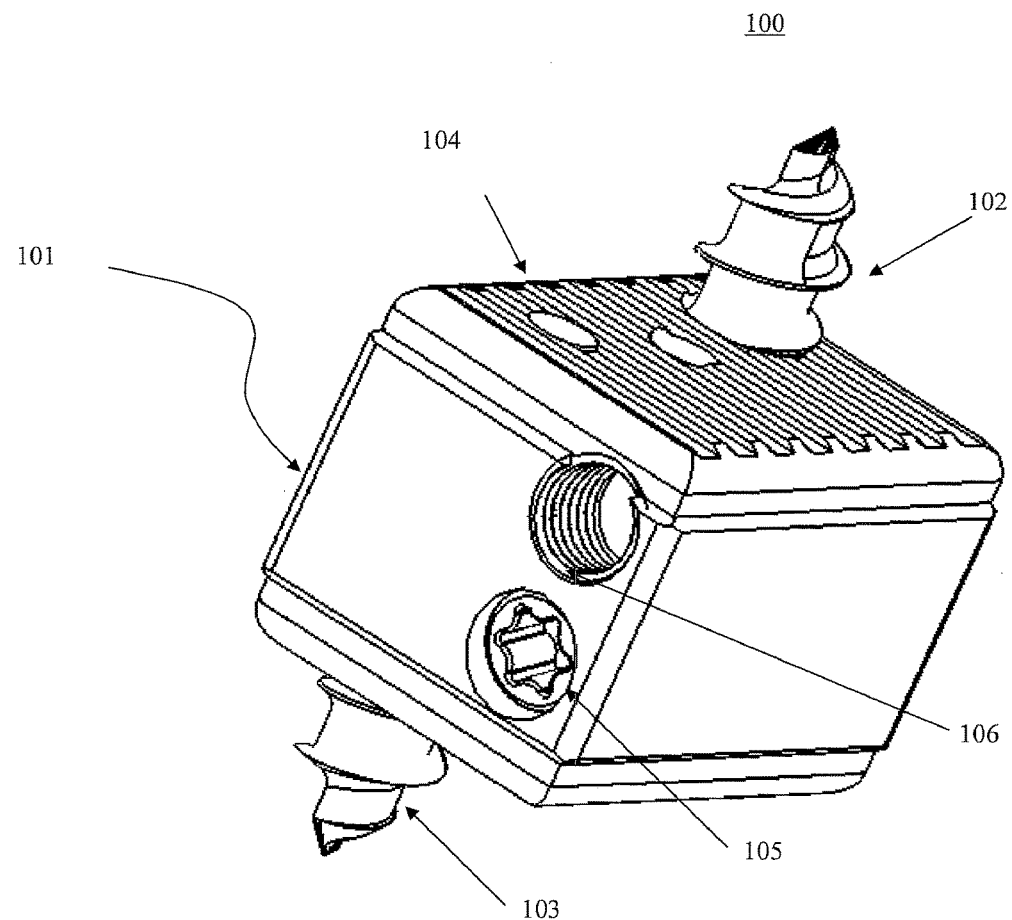
FIG. 1A illustrates an isometric view of the universal bidirectional screw (UBS) alternatively referred to as the bi-directional fixating transvertebral screw (BDFT).
Figure 1B:
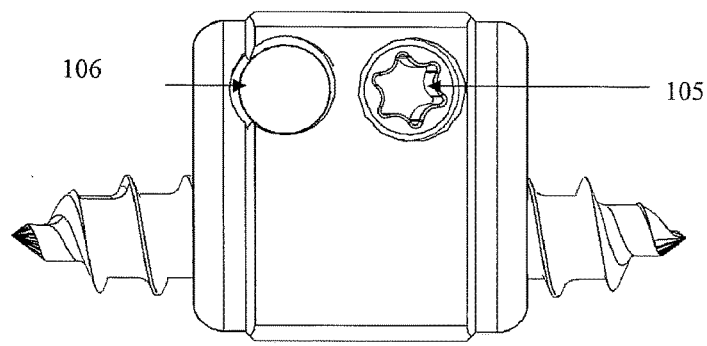
FIG. 1B illustrates the lateral view of the UBS (BDFT) with rostral and caudal screws partially extended.
Figure 1C:
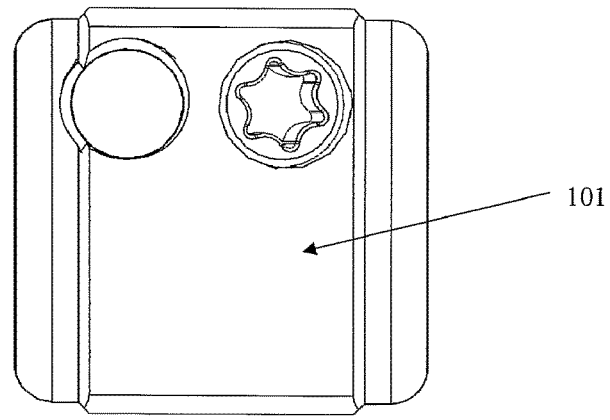
FIG. 1C illustrates the lateral view of the UBS (BDFT) with the screws withdrawn.
Figure 2:
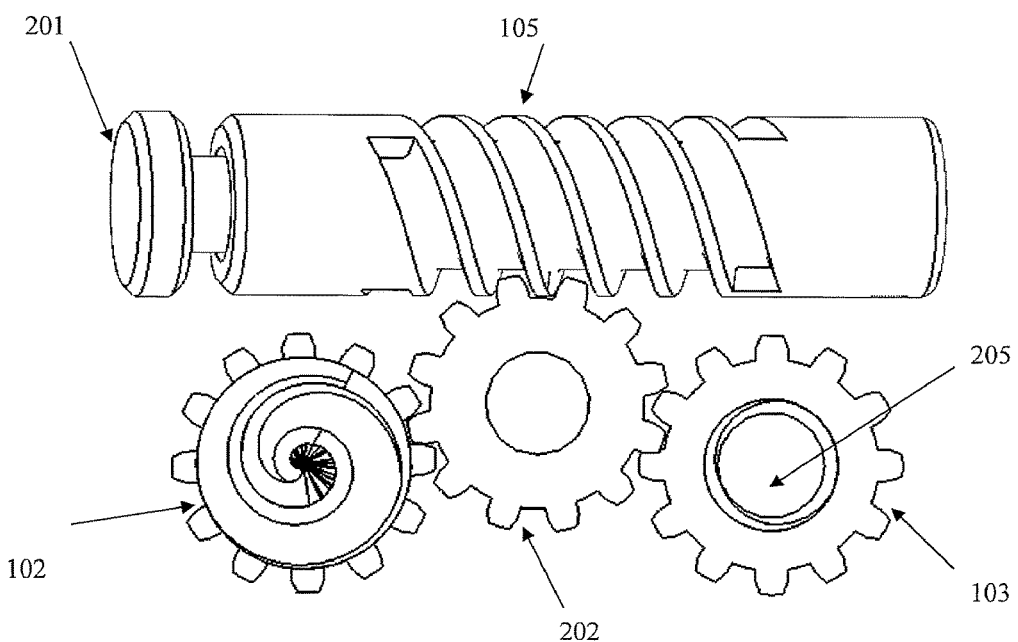
FIG. 2 illustrates a front view of the UBS (BDFT) without the gear box and cover.
Figure 3A:
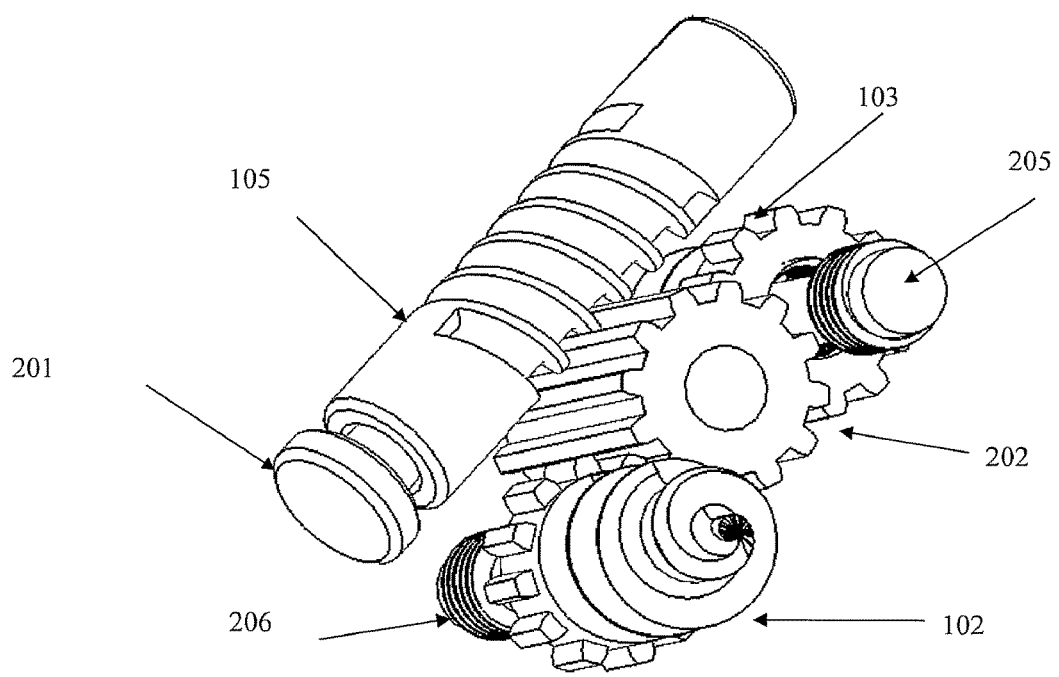
FIGS. 3A and 3B illustrate perspective, and exploded perspective views, respectively, of the UBS (BDFT) without gear box and cover, with the screws fully extended.
Figure 3B:
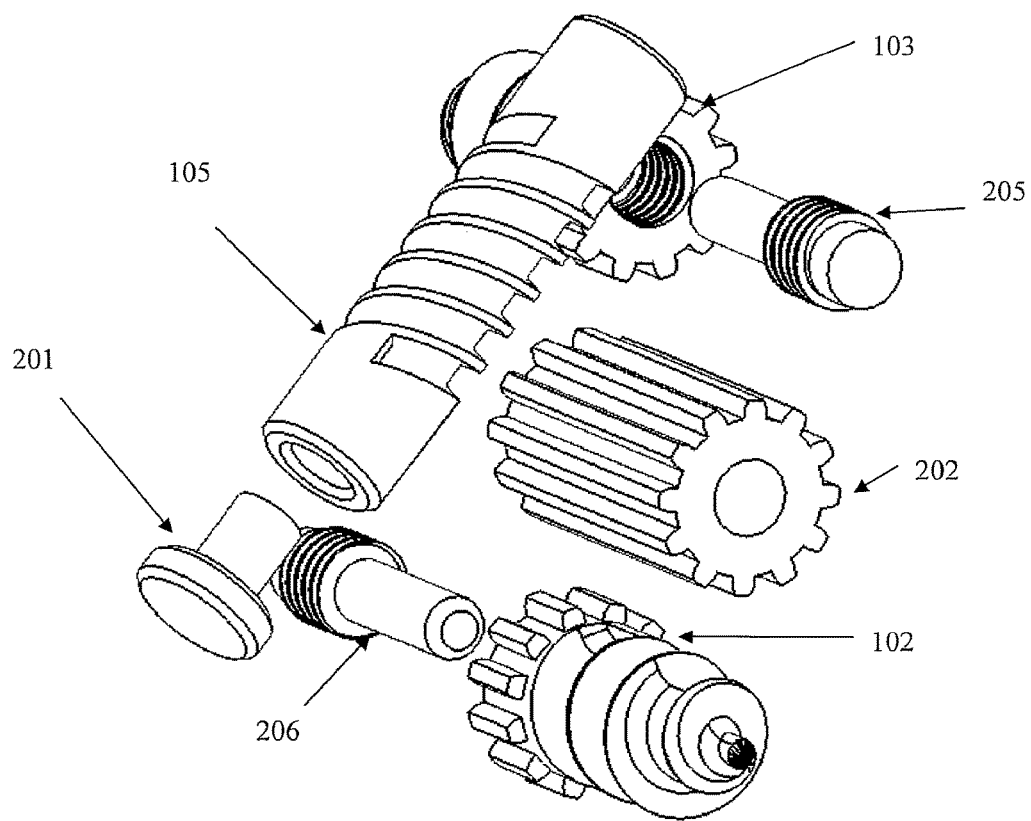
Figure 4:
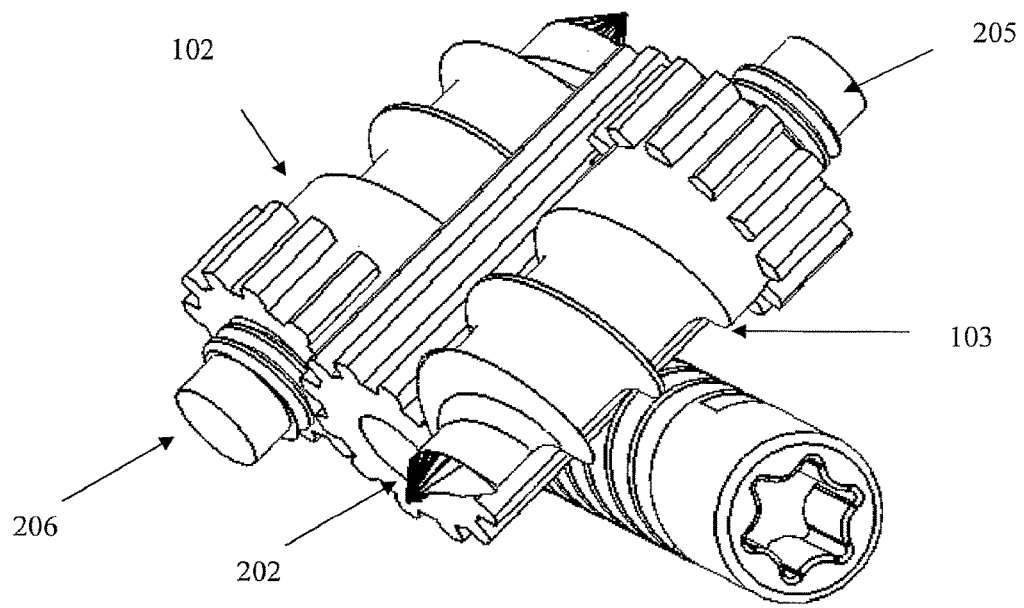
FIG. 4 illustrates a perspective view of the UBS (BDFT) without the gear box and cover, with screws partially extended.

FIGS. 1A through 1C illustrate three-dimensional views of the UBS/BDFT screw 100. All its inner components are in the gear box casing 101. The internal mechanisms are illustrated in FIGS. 2-5C. FIG. 1A illustrates the isometric view of the UBS 100 showing the outer gear box 101 containing the external mechanism, with superior screw 102 and inferior screw 103 extended. There are serrations 104 on the superior and inferior surfaces of the box 101 intended to integrate with the surface of the superior and inferior vertebral body surfaces. The gear box 101 which is made either of PEEK (polyethylene-ketol) or titanium acts as a column preventing subsidence of the disc space. Also seen are the surface of the worm drive screw 105, and the horizontal mini-plate screw insert 106 for capping the horizontal mini-plate to the gear box's 101 surface (FIGS. 1A-C and 6A-C).

FIGS. 1-4 illustrate the inner components of the BDFT/UBS 100 without the enclosing gear box 101. The inner components include a single wormed drive screw 105, a drive spindle 201, a spur gear 202, superior screw 102 and inferior screw 103 with superior and inferior screw spindles 205, 206 (FIGS. 1-4). The mechanism of operation is thus: The wormed drive screw 105 is rotated clockwise. This rotation in turn rotates the spur gear 202. The spur gear 202 interdigitates with the superior screw 102 on one side and the inferior screw 103 on the other side. Rotation of the spur gear 202 leads to simultaneous rotation of the superior and inferior screws 102, 103 in equal and opposite directions. The spindles in the wormed drive screw 105 and the superior and inferior screws 102, 103 maintain the axis of screw orientation. The screws 102, 103 are self drilling and hence there is no need for bony preparation.

Figure 5A:
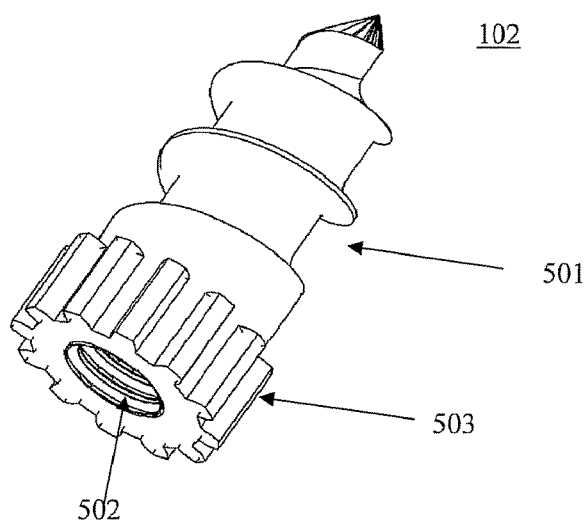
FIG. 5A illustrates a perspective view of a single insertion screw of the BDFT.
Figure 5B:
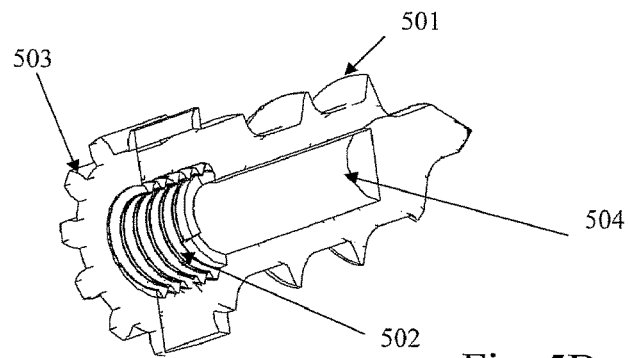
FIG. 5B illustrates a perspective cross-sectional view of a BDFT insertion screw.

FIGS. 5A and 5B illustrate in perspective and cross-sectional views the detailed elements of the superior and inferior screws 102, 103. These figures illustrate the external threading 501, the internal threading 502, the spindle socket and the spur gear teeth 503 which interdigitate with the spur gear 202. The screws 102, 103 are self drilling as noted.

Figure 5C:
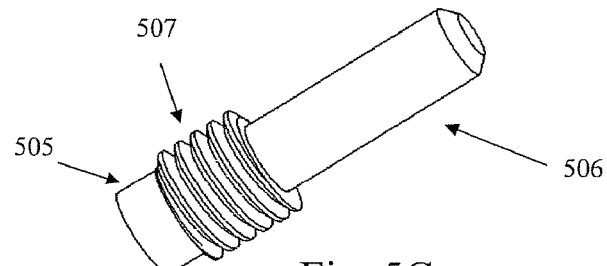
FIG. 5C illustrates a perspective view of the spindle.

FIG. 5C illustrates the details of the spindle including its base 505, its rod 506 and its threaded segment 507.

Figure 6A:
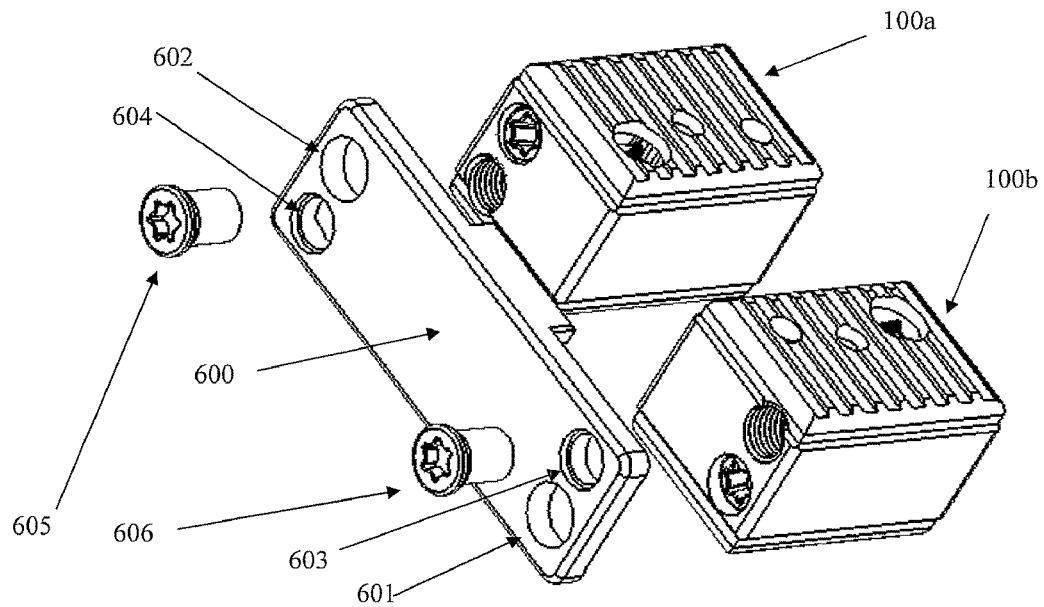
FIG. 6A illustrates an exploded view of the two-in-one design consisting of two BDFT screws and a horizontal mini-plate.
Figure 6B:
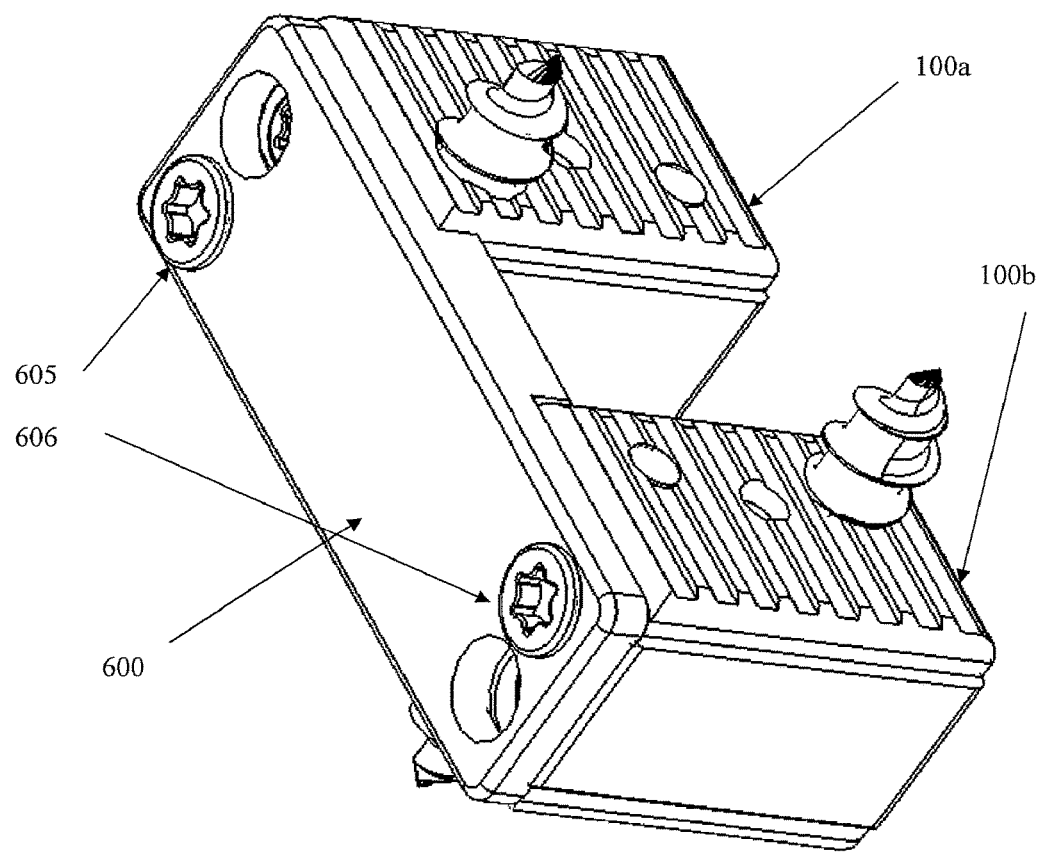
FIG. 6B illustrates the two-in-one design with the horizontal mini-plate secured and the screws extended.
Figure 6C:
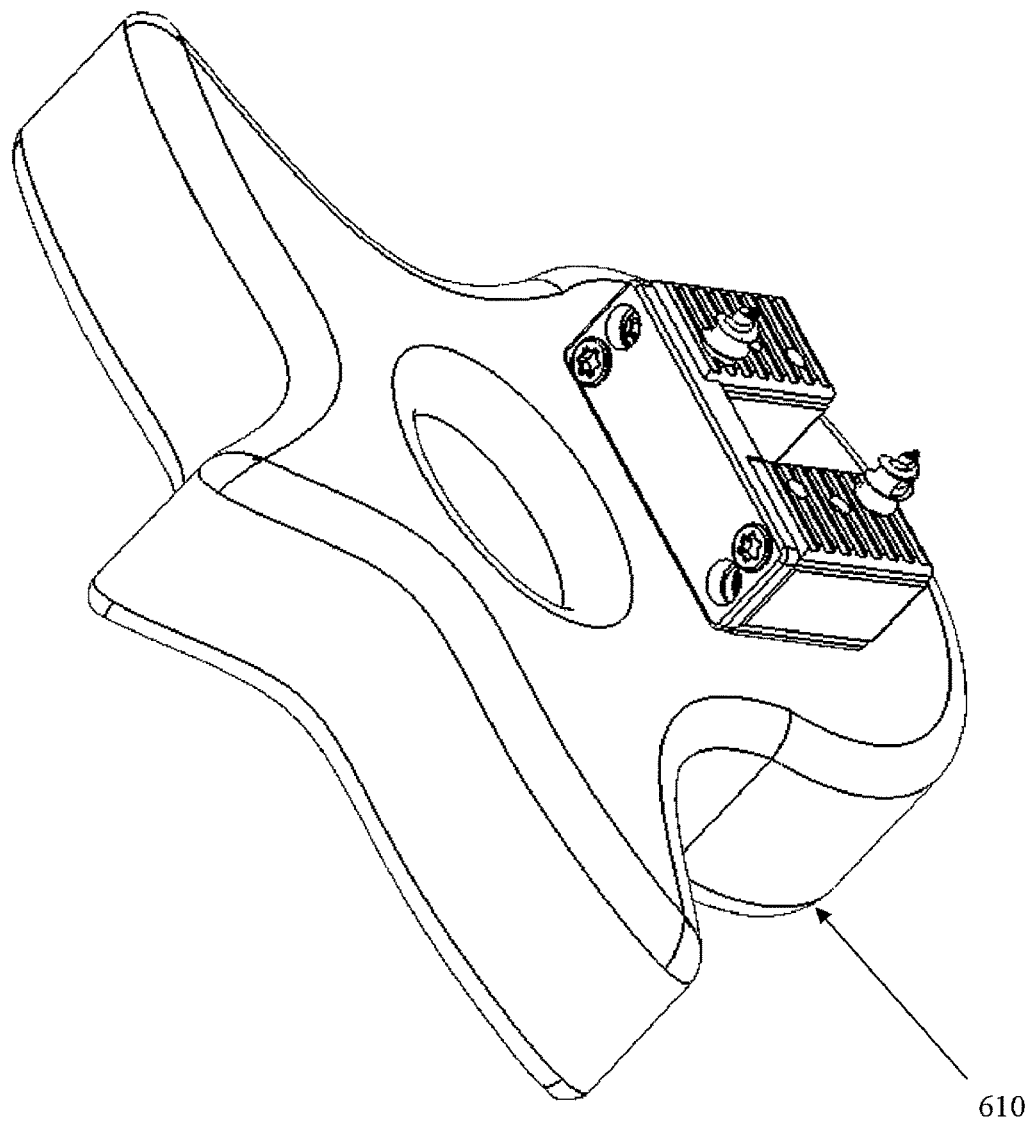
FIG. 6C illustrates the two-in-one design, and its position with respect to the vertebral body.

FIGS. 6A-6C illustrate the two-in-one design concept. This design concept includes two UBS/BDFT screws 100*a*, 100*b* which are placed in the left and right portions of the intervertebral disc space, which are then capped by a horizontal mini-plate 600. Note how the mini-plate has four perforations 601, 602, one on each side to allow entry of the wormed screw drive into the gear box. There are an additional two perforations 603, 604, one on each side, to secure the plate to the two UBS boxes 100*a*, 100*b* with plate screw caps 605, 606. FIG. 6C demonstrates the position of the two-in-one system with respect to the vertebral body 610. In between the two BDFT/UBS screws 100*a*, 100*b*, bone fusion material is inserted. The horizontal mini-plate 600 prevents the bone from growing into the nerves above it. With this system it is also possible to place a third screw inferior and in the middle of the two other UBS screws 100*a*, 100*b* thereby providing additional screw intervertebaral fixation.

Figure 7A:
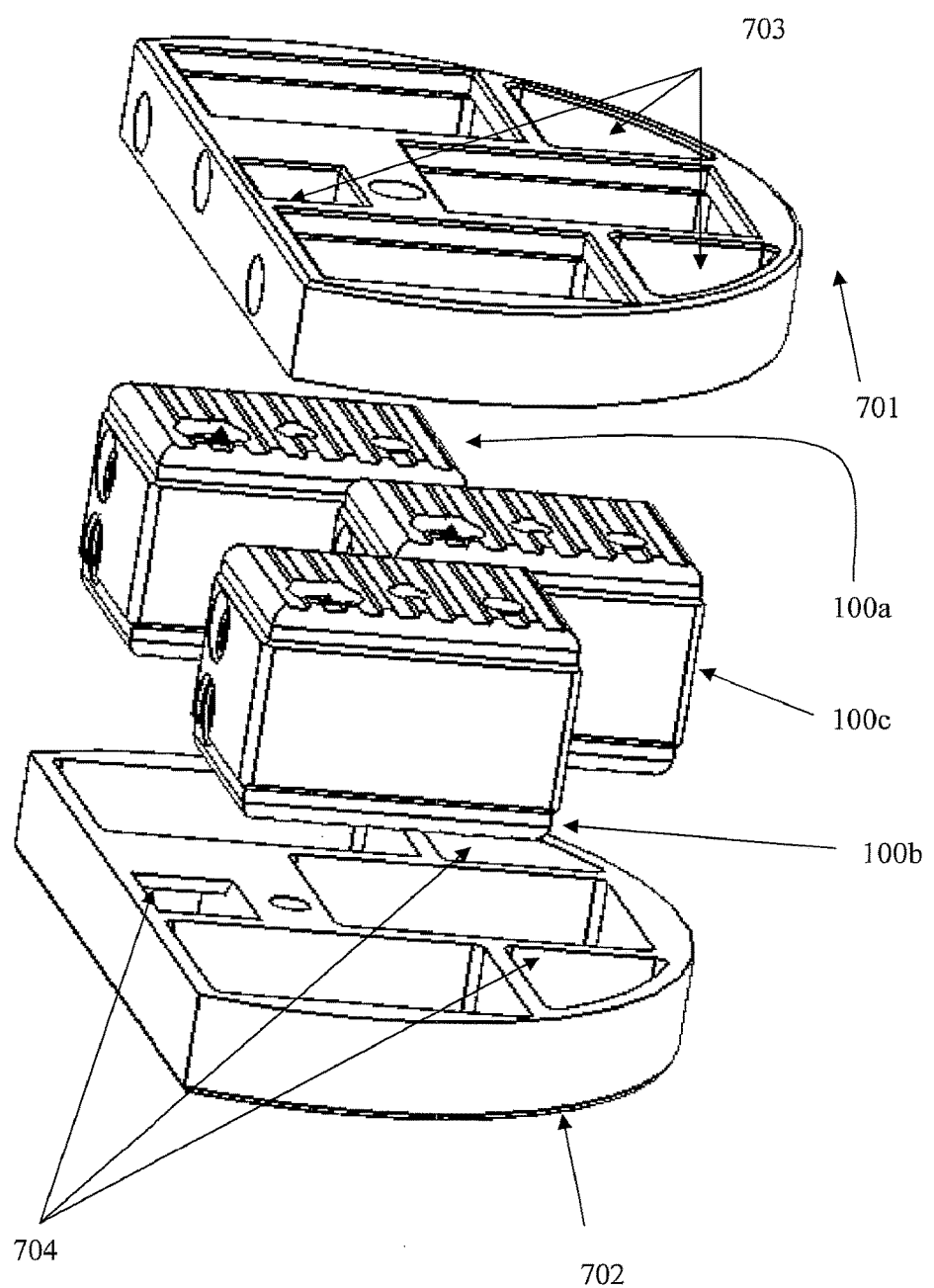
FIG. 7A illustrates an exploded view of the three-in-one system (IBFD) which consists of three BDFT screws in an enclosure system.
Figure 7B:
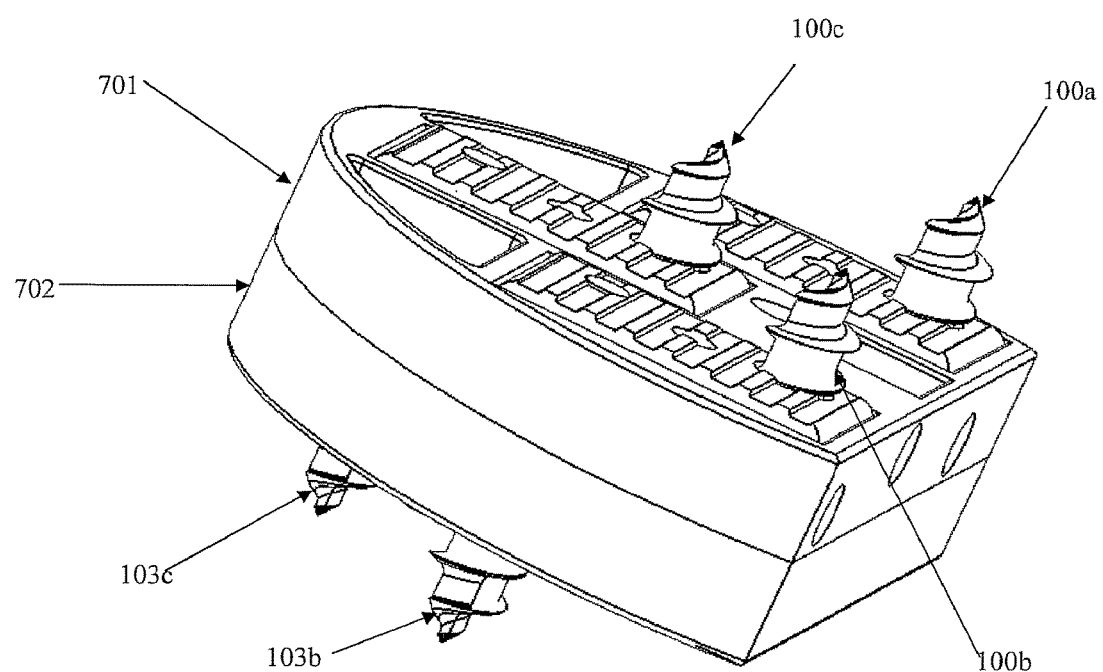
FIG. 7B illustrates the three-in-one system (IBFD) with screws extended.
Figure 7C:
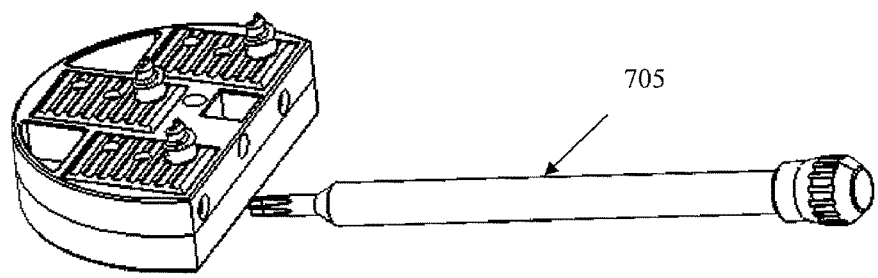
FIG. 7C illustrates the IBFD with an accompanying screw driver.

FIGS. 7A through 7C illustrate the three-in-one design otherwise known as the IBFD. This device consists of five components. Three UBS/BDFT screws 100*a*, 100*b*, 100*c*, a superior and an inferior enclosure 701, 702. The enclosures 701, 702 are attached to the UBS/BDFT screws 100*a*, 100*b*, 100*c*. A screw driver 705 is used to actuate the screws 100*a*, 100*b*, 100*c*. There are also slots 703, 704 for bone fusion material. This device is only for anterior insertion into the spine, and it covers the entire cross-sectional area of the interspace, and is thus a total IBFD. The enclosures can be made out of PEEK, titanium, cobalt chromium or any other similar substance. The structure of the device provides significant three column stability and prevents subsidence of the construct.

Figure 8A:
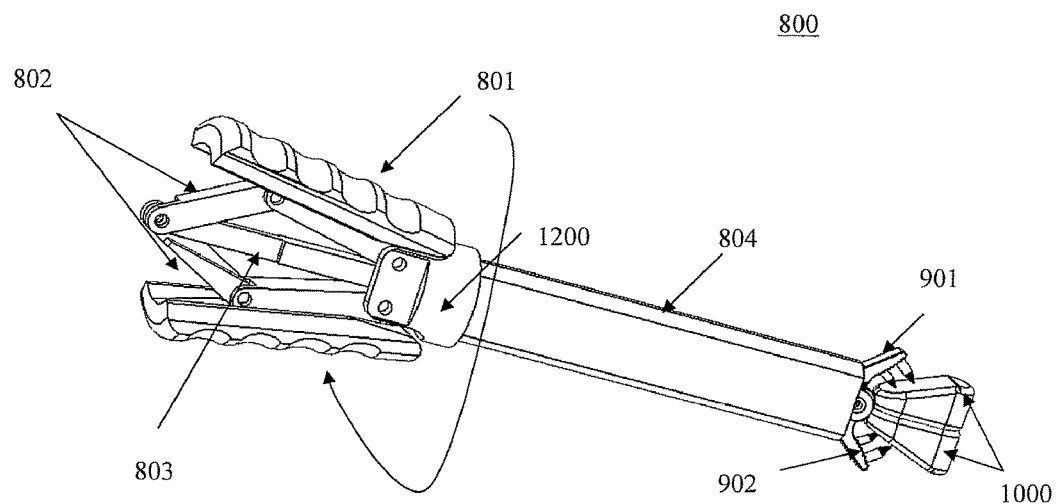
FIGS. 8A and 8B illustrate perspective, and cross-sectional views of the interarticular joint stapling device with staple, respectively.
Figure 8B:
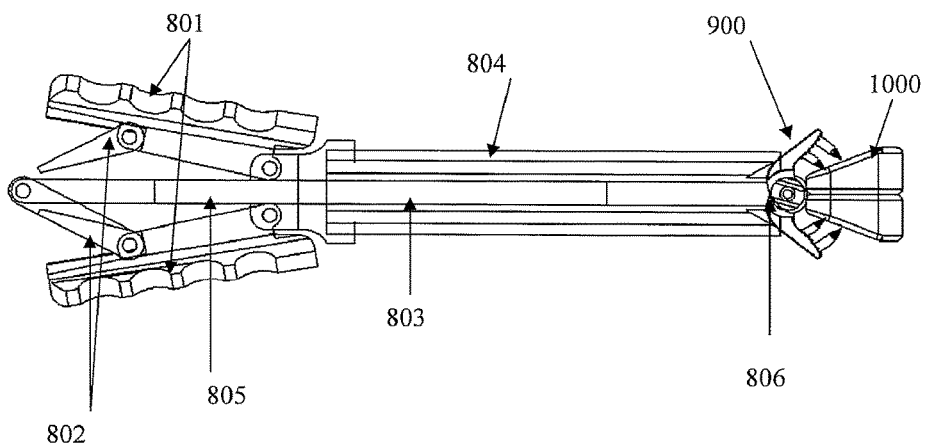

FIGS. 8A and 8B illustrate the individual components of the facet joint staple gun 800. It consists of a remote action mechanism which includes grip handles 801, transmission linkages 802, a drive rod 803, a cylinder 804. The drive rod 803 has a force end 805 and an action end 806.

Figure 9A:
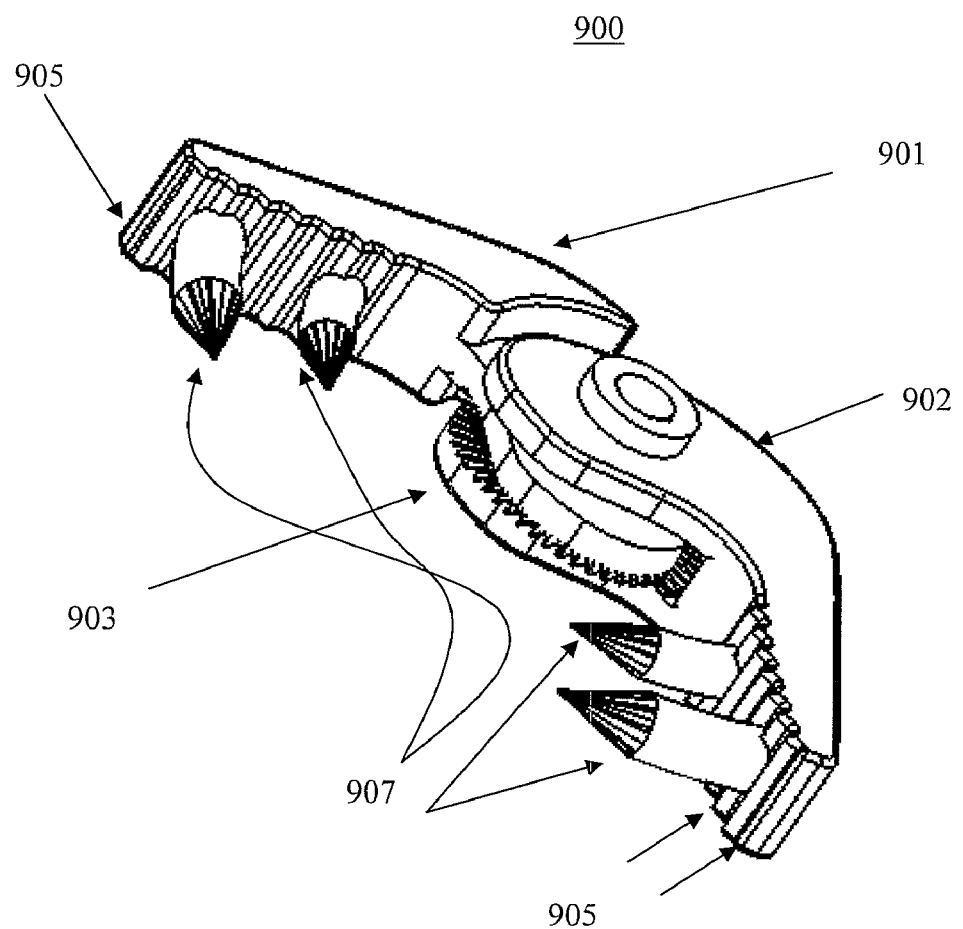
FIGS. 9A and 9B illustrate perspective and exploded views of the staple, respectively.
Figure 9B:
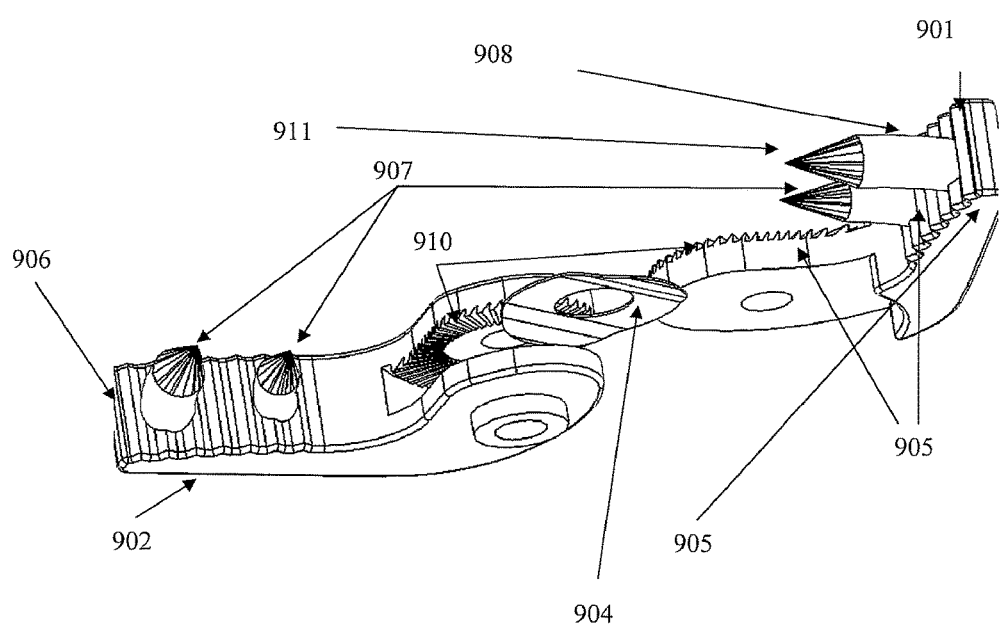
Figure 10:
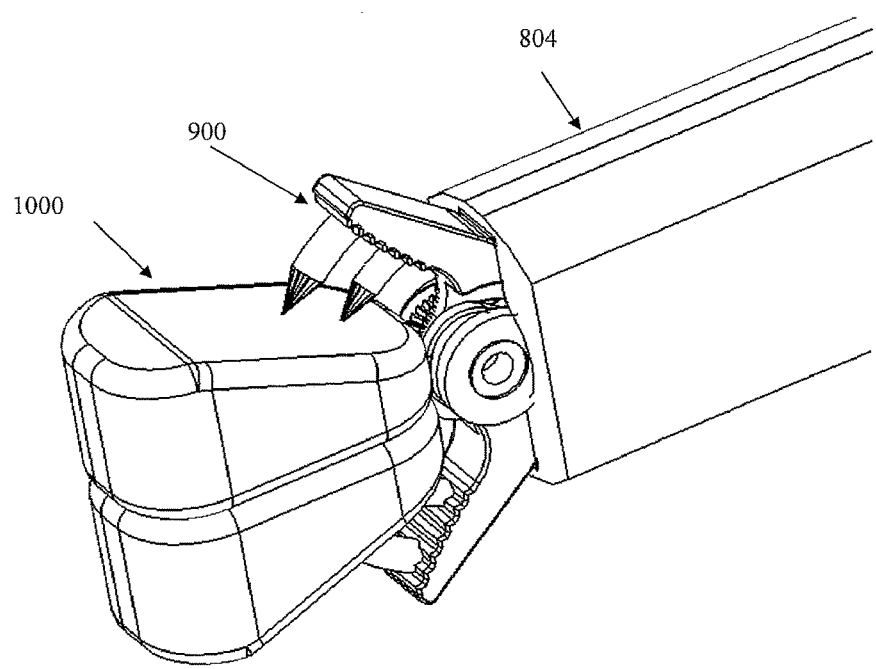
FIG. 10 illustrates a perspective view of the staple gun engaging the facet joint.

FIGS. 9A and 9B illustrate the details of the facet joint stapler. The staple 900 has superior and inferior staple segments 901, 902. These segments 901, 902 are joined by a teethed unidirectional locking mechanism 903 having right triangular teeth 910, and a spring washer 904. The inferior surfaces 905, 906 of each staple segment 901, 902 are serrated to facilitate bony integration, and each segment has two bone piercing elements 907 with a base 908. FIG. 10 illustrates the staple 900 in the staple gun 800, in the opened position engaging the facet joints, prior to penetration and stapling.

Figure 11:
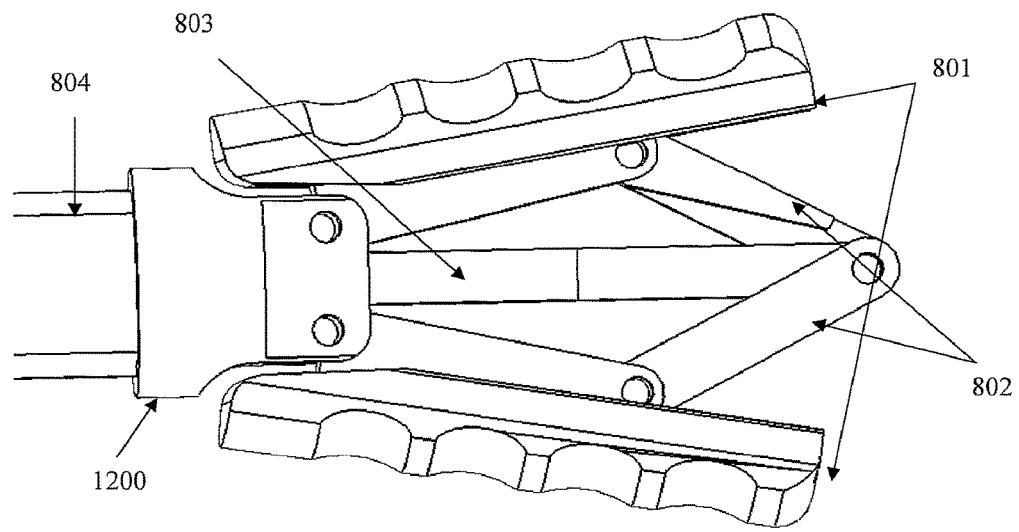
FIG. 11 illustrates the remote action mechanism of the staple gun.
Figure 12A:
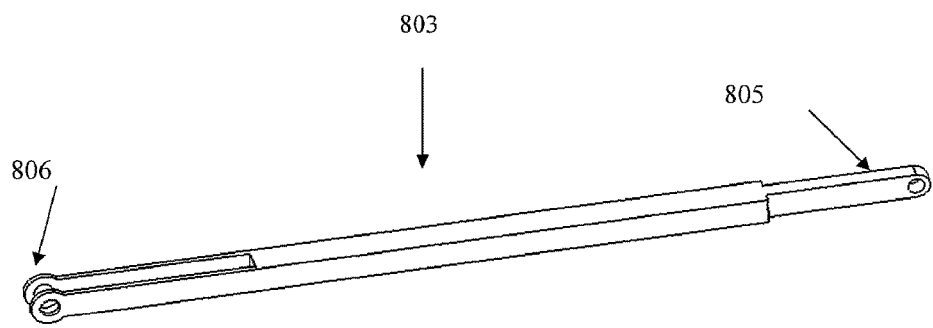
FIG. 12A illustrates the drive rod.
Figure 12B:
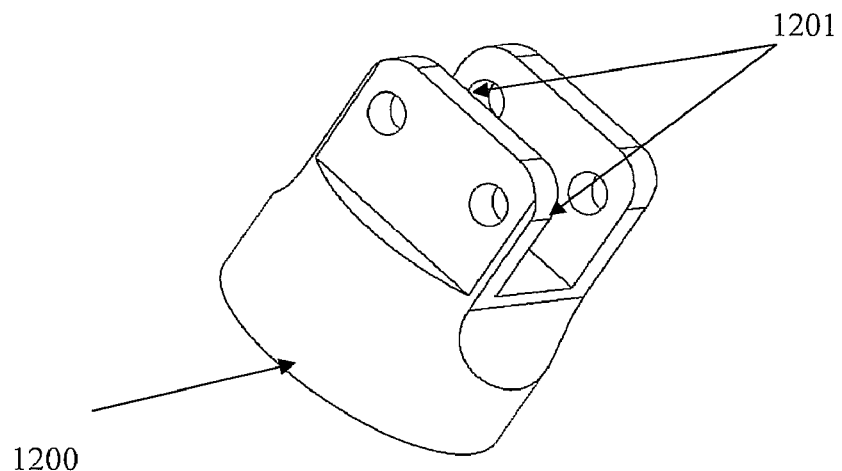
FIG. 12B illustrates the fulcrum cylinder connector.
Figure 12C:
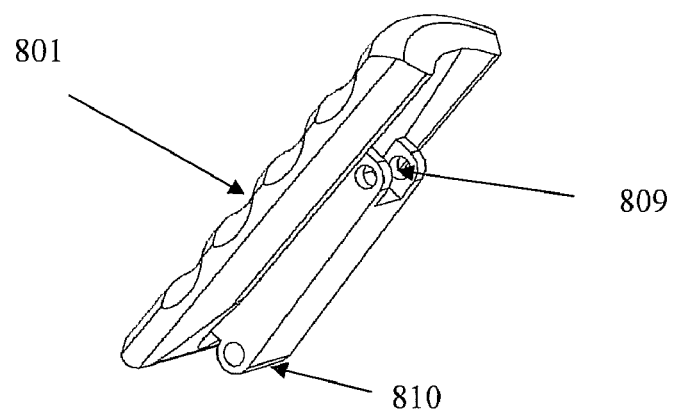
FIG. 12C illustrates the grip handle.
Figure 12D:
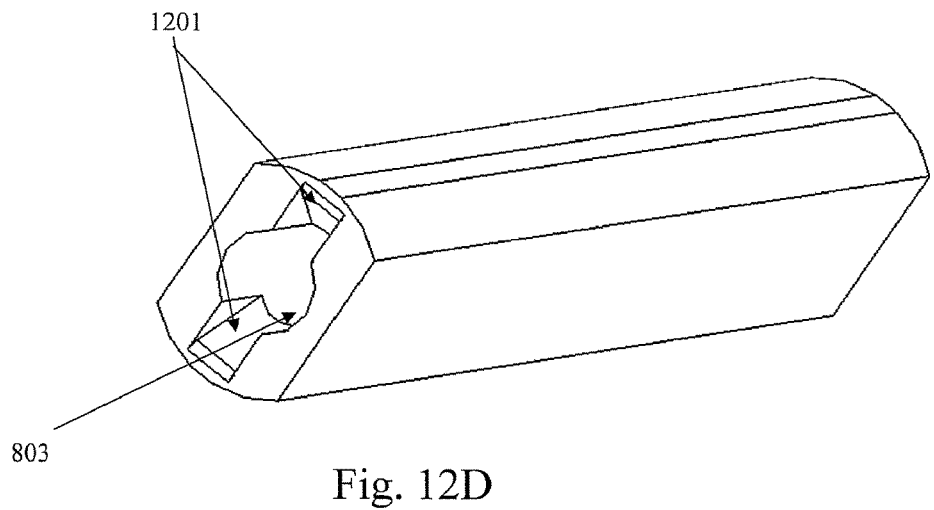
FIG. 12D illustrates the cylinder.
Figure 12E:
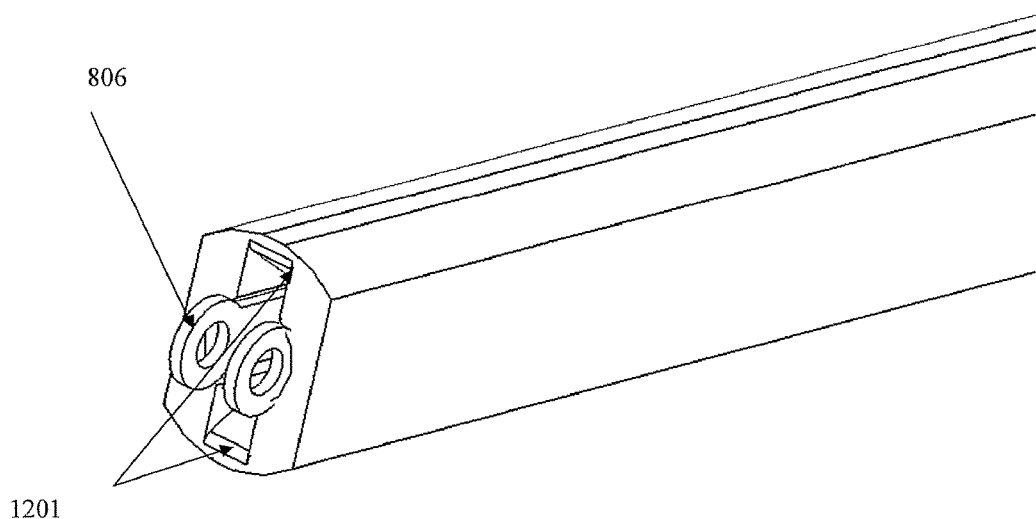
FIG. 12E illustrates the cylinder with the drive rod.
Figure 13:
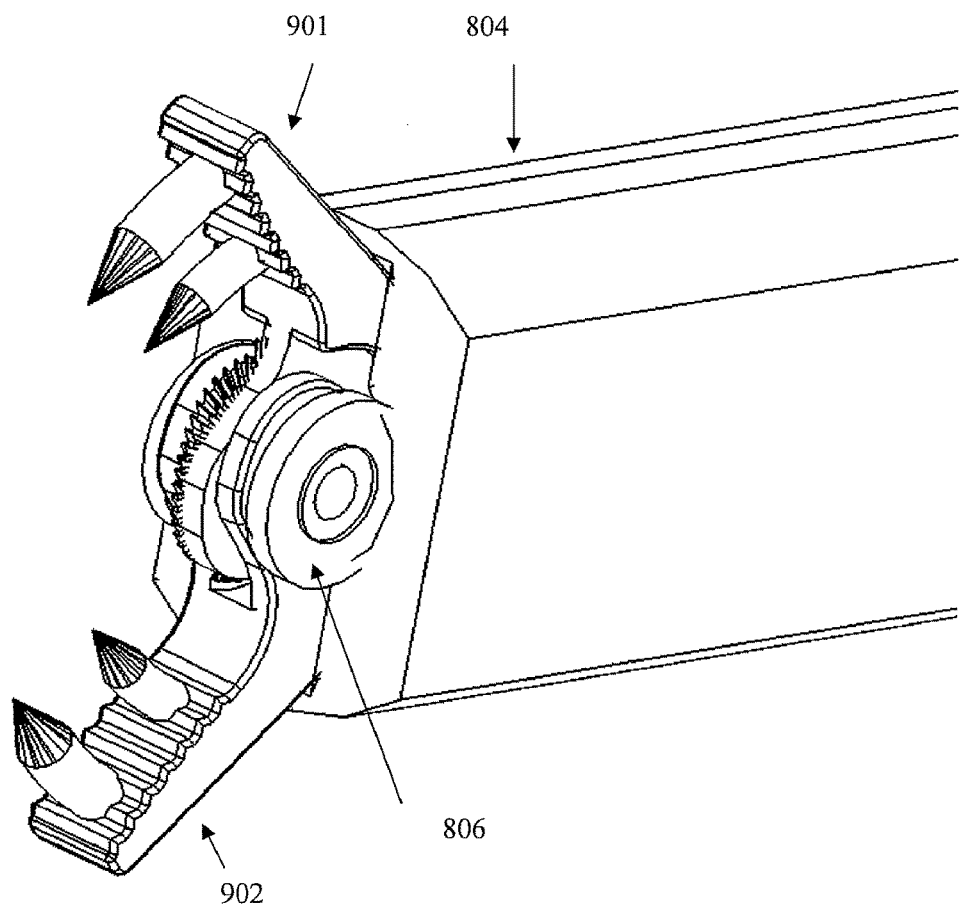
FIG. 13 illustrates the drive and insertion mechanism of the staple.

FIGS. 11-13 illustrate the different components of the staple gun 800 and staple 900 in a detailed manner. The mechanism of action of the staple gun 800 includes engaging the staple 900 in the action end 806 of the drive rod 803 and resting in the staple guide chamfers 1201 (FIGS. 12A-13). When the staple 900 is thus engaged in the staple gun 800, the grip handles 801 are squeezed together, bringing the linkages 802 together (FIGS. 11-12C). This action is transmitted to the force end 805 of the driving rod 803 which moves upwards. This leads to upward movement of the action end 806 of the drive rod 803 in which the staple 900 is nestled, leading to the opposition of the superior and inferior segments 901, 902 of the staple, 900 and the penetration of the pins 907 into the bone. The distance of bone penetration is modulated by the pressure put on the hand grips 801. Hence graded facet joint opposition leading to different degrees of opposition and hence rigidity can be accomplished. The greater the force the greater the opposition. Thus this is a modulated not a static stapling mechanism.

2. The Surgical Method

The surgical steps necessary to practice the present invention will now be described.

The posterior lumbar spine implantation of the BDFT (UBS) screws 100, horizontal mini-plate 600 and IBFD 100a, 100b, 100c can be implanted via previously described posterior lumbar interbody fusion (PLIF) or posterior transforaminal lumbar interbody fusion (TLIF) procedures. The procedure can be performed open, microscopic, closed, tubular or endoscopic. Fluoroscopic guidance can be used with any of these procedures.

After the adequate induction of anesthesia, the patient is placed in the prone position.

A midline incision is made for a PLIF, and one or two parallel paramedian incisions or a midline incision is made for a TLIF. For the PLIF a unilateral or bilateral facet sparing hemi-laminotomy is created to introduce the BDFT (UBS) screws 100, into the disc space after it is adequately prepared. For the TLIF procedure, after a unilateral dissection and drilling of the inferior articulating surface and the medial superior articulating facet, the far lateral disc space is entered and a circumferential discectomy is performed. The disc space is prepared and the endplates exposed.

There are then multiple embodiments to choose from for an intervertebral body fusion. With the first and simplest choice, under direct or endoscopic guidance one. Two or three BDFT screws 100 can be placed. If two screws 100 are placed. One is placed on the right, and one on the left. If three are placed, the additional one can be placed more anterior and midline, such that the three screws 100a, 100b, 100c form a triangulation encompassing the anterior and middle columns of the vertebral bodies. (FIGS. 6B and 6C). Once the screws 100 are placed into the desirable intervertebral body positions, the worm drive screws 105 are turned clockwise which leads to the penetration and engagement of the superior and inferior bi-directional screws 102, 103 into the vertebral bodies above and below. BDFT screws can also be placed in angled positions if desirable (not illustrated). Bone material or alternative intervertebral fusion material can then be packed into the disc space around the BDFTs 100. The casing gear box 101 of the screws prevents subsidence of the vertebral bodies (FIGS. 1A-C). An additional option in the posterior lumbar spine is to place a horizontal mini-plate 600 underneath the thecal sac to prevent bone migration into the nerves. This plate 600 (FIGS. 6A-C) can be slid underneath the thecal sac, and secured to the right and left BDFT (UBS) screws 100. Once set, the plate 600 can be locked down with plate screw caps 606 thereby preventing movement (FIGS. 6A-C).

If further posterior column stability or rigidity is required, unilateral or bilateral, single level or multiple level facet screw stapling 900 can be performed under open, microscopic flouroscopic or endoscopic vision. Radiographic confirmation of staple position is obtained. Calibrated stapling leads to opposition of the facet joints 1000 with incremental degrees of joint opposition. This can lead to variable degrees of posterior column rigidity and/or flexibility (FIGS. 8-13).

The anterior cervical, thoracic and lumbar spine implantation of one, two or three UBS (BDFT) screws 100 can be performed in a similar manner to posterior application. Likewise a horizontal mini-plate 600 can be used to cap two BDFT screws 100. Anterior placement of the three-in-one device (IBFD) 100a, 100b, 100c into the L4/5 and L5/S1 interspaces can be performed on the supine anesthetized patient via previously described open micropscopic or endoscopic techniques. Once the disc space is exposed and discectomy and space preparation is performed, placement of one, two or three BDFT screws 100 with or without a mini-plate 600, or placement of the IBFD 100a, 100b, 100c is identical to that performed for the posterior approach.

The posterior placement of the BDFT screws 100 alone or combined with horizontal mini-plates (two-in-one) 600 or with IBFD 100a, 100b, 100c into the thoracic spine can be performed via previously described transpedicular approaches; open or endoscopic. The anterior placement of the IBFD (three-in-one) into the thoracic spine can be accomplished via a trans-thoracic approach. Once disc space exposure is obtained via either approach, all of the above mentioned embodiments can be inserted. Engagement of the devices is identical to what was mentioned above.

For anterior placement of the cervical embodiments of the BDFT screw(s) 100 with or without the horizontal cervical mini-plate 600, and the IBFD 100a, 100b, 100c embodiment, the anterior spine is exposed in the anesthetized patient as previously described for anterior cervical discectomies. Once the disc space is identified, discectomy is performed and the disc space prepared. Implantation and engagement of all devices is identical to that described for the anterior lumbar and thoracic spines.

The present invention may provide an effective and safe technique that overcomes the problems associated with current tanspedicular-based thoracic and lumbar fusion technology, and with current vertical cervical plating technology, and for many degenerative stable and unstable spine diseases, and could replace many pedicle screw-based and anterior vertical-plate based instrumentation in many but not all degenerative spinal conditions. Calibrated facet joint screw staples 900 can facilitate flexible fusions and could replace current static trans-facet screws.

To our knowledge there has not been any other previously described bi-directional screw 100 for use in the spine, other joints, or for any commercial or carpentry application. The bi-directional screw 100 described herein may indeed have applications in general commercial, industrial and carpentry industries. To our knowledge the description of zero to subzero profile anterior or posterior horizontal spinal plates which traverse the diameter of the disc space has not been previously described. To our knowledge an intervertebral three-in-one construct 100a, 100b, 100c has not been previously reported. To our knowledge calibrated facet joint staples 900 have not been previously described.

We claim:

1. A stapling apparatus for a staple having rotatable segments, the stapling apparatus comprising:
   a cylinder;
   a drive rod disposed within the cylinder, said drive rod having first and second ends;
   a pair of grip handles disposed at a first end of the cylinder;
   a linkage coupling the grip handles to the first end of the drive rod; and
   a coupling mechanism disposed at the second end of the drive rod;
   wherein when the grip handles are forced together, the linkage imparts motion to the drive rod and the coupling mechanism and moves the drive rod and the coupling mechanism in a direction toward the first end of the cylinder,
   wherein the staple is a bone piercing staple,
   wherein the coupling mechanism is configured to grasp the bone piercing staple at the second end of the cylinder,
   wherein when the grip handles are forced together, the linkage imparts motion to the drive rod and the coupling mechanism and moves the drive rod and the coupling mechanism in the direction toward the first end of the cylinder such that at least a portion of the coupling mechanism moves into an opening at the second end of the cylinder such that at least a portion of the bone piercing staple moves into the opening with the portion of the coupling mechanism and such that the rotatable segments of the bone piercing staple are forced toward each other by the second end of the cylinder.

2. The stapling apparatus according to claim 1 which further includes a fulcrum that is disposed at the first end of the cylinder and coupled to the linkage.

3. The stapling apparatus according to claim 1, wherein the staple comprises:
   a first rotatable segment having a plurality of bone piercing elements, disposed on serrated surfaces;
   a second rotatable segment having a plurality of bone piercing elements, disposed on serrated surfaces; and
   a unidirectional locking mechanism coupled to the first and second rotatable segment, that permits the first and second rotatable segments to rotate about a pivot point, said unidirectional locking mechanism including a plurality of teeth.

4. The stapling apparatus according to claim 3, wherein the unidirectional locking mechanism includes a lock washer and the teeth include right angled surfaces.

5. The stapling apparatus according to claim 4, wherein the bone piercing elements include a pointed end and a base which is disposed on the serrated surfaces.

6. The stapling apparatus of claim 1, wherein each of the pair of grip handles is disposed on an opposite side of a longitudinal axis of the cylinder and the drive rod.

7. The stapling apparatus of claim 6, wherein, when the pair of grip handles are forced together, each of the pair of grip handles moves closer to the longitudinal axis of the cylinder and the drive rod.

8. The stapling apparatus of claim 6, wherein the first end of the drive rod is disposed between the pair of grip handles.

9. The stapling apparatus of claim 1, wherein the cylinder includes a slot at an entrance to the opening of the cylinder at the second end of the cylinder, and
   wherein, when the pair of grip handles are forced in the direction toward each other, the linkage imparts motion to the drive rod and moves the drive rod in the direction toward the first end of the cylinder such that at least a portion of the mechanism moves into the slot at the second end of the cylinder.

10. The stapling apparatus of claim 1, wherein the linkage includes:
    a first linkage having a first end rotatably coupled to a first handle of the pair of grip handles and a second end rotatably coupled to the first end of the drive rod;
    a second linkage having a first end rotatably coupled to a second handle of the pair of grip handles and a second end rotatably coupled to the first end of the drive rod.

11. The stapling apparatus of claim 1, wherein each of the pair of grip handles is disposed on an opposite side of a longitudinal axis of the cylinder and the drive rod.

12. The stapling apparatus of claim 11, wherein, when the pair of grip handles are forced in the direction toward each other, each of the pair of grip handles moves closer to the longitudinal axis of the cylinder and the drive rod.

13. The stapling apparatus of claim 1, wherein the first end of the drive rod is disposed between the pair of grip handles.

14. A system comprising the stapling apparatus of claim 1 and a staple.

15. The system of claim 14, wherein the staple comprises means for piercing bone, means for joining the means for piercing bone, and means for locking the means for joining, and wherein the stapling apparatus comprises means for guiding the staple.

16. A stapling apparatus and staple assembly for joining facets, the stapling apparatus and staple assembly comprising:
    a staple comprising:
    a first rotatable segment having a plurality of bone piercing elements, disposed on serrated surfaces;
    a second rotatable segment having a plurality of bone piercing elements, disposed on serrated surfaces; and
    a unidirectional locking mechanism that prevents the first and second rotatable segments from rotating in a first direction about a pivot point and permits the first and second rotatable segment to rotate in a second direction about the pivot point, the second direction being opposite the first direction, said unidirectional locking mechanism including a plurality of teeth; and
    a stapling apparatus comprising:
    a cylinder having a first end and a second end, the cylinder having an opening extending from the first end to the second end;
    a pair of grip handles disposed at the first end of the cylinder;

a linkage coupling each handle of the pair of grip handles to the first end of the drive rod; and a drive rod disposed in and extending through the opening in the cylinder from the first end of the cylinder to the second end of the cylinder, wherein the drive rod has a first end and a second end, the first end of the drive rod being adjacent the first end of the cylinder and the second end of the drive rod being adjacent to the second end of the cylinder, wherein the drive rod includes a coupling mechanism at the second end for grasping the staple, wherein, when the pair of grip handles are forced in a direction toward each other, the linkage imparts motion to the drive rod and moves the drive rod in a direction toward the first end of the cylinder, wherein the coupling mechanism grasps the staple at the second end of the cylinder, wherein, when the pair of grip handles are forced in the direction toward each other, the linkage imparts motion to the drive rod and the coupling mechanism and moves the drive rod and the coupling mechanism in the direction toward the first end of the cylinder such that at least a portion of the coupling mechanism moves into the opening at the second end of the cylinder and at least a portion of each of the first rotatable segment and the second rotatable segment of the staple moves into the opening whereby the first and second rotatable segments of the staple are forced toward each other by the second end of the cylinder.

\* \* \* \* \*